(12) United States Patent
Beckmann et al.

(10) Patent No.: US 6,458,538 B1
(45) Date of Patent: Oct. 1, 2002

(54) METHODS OF ASSAYING FOR COMPOUNDS THAT INHIBIT PREMATURE TRANSLATION TERMINATION AND NONSENSE-MEDIATED RNA DECAY

(75) Inventors: Holger Beckmann, El Cerrito, CA (US); Marc Learned, El Granada, CA (US); Stuart Peltz, Piscataway, NJ (US); Kevin Czaplinski, Summerset, NJ (US)

(73) Assignees: PTC Therapeutics, Inc., Piscataway, NJ (US); Tularik Incorporated, South San Francisco, CA (US)

( * ) Notice: Subject to any disclaimer, the term of this patent is extended or adjusted under 35 U.S.C. 154(b) by 0 days.

(21) Appl. No.: 09/461,508

(22) Filed: Dec. 14, 1999

(51) Int. Cl.⁷ ................................................ C12Q 1/68
(52) U.S. Cl. .............................. 435/6; 435/7.21; 435/8; 435/24; 435/28; 435/29; 435/69.1; 435/320.1; 435/325; 435/455; 536/23.5
(58) Field of Search ............................. 435/6, 29, 7.21, 435/8, 24, 28, 325, 320.1, 69.1, 455; 536/23.5

(56) References Cited

U.S. PATENT DOCUMENTS 5,840,702 A  * 11/1998 Bedwell ....................... 514/23
6,071,700 A  *  6/2000 He et al. ........................ 435/6

OTHER PUBLICATIONS

Carter er. al.; A splicing–dependent regulatory mechanism that detects translation signals, 1996, The EMBO Journal vol. 15, No. 21: 5965–5975.*
Dinman er. al.; Translating old drugs into new treatment: ribosomal frameshifting as a target for antiviral agents, 1998, TIBTECH vol. 16: 190–196.*
Carter et. al.; A Regulatory Mechanism That Detects Premature Nonsense Codons in T–Cell Receptor Transscripts in Vivo Is Reversed by Protein Synthesis Inhibitors in Vivo, 1995, The Journal of Biological Chemistry vol. 270, No. 48: 28995–29003.*
Burbaum et. al.; New technologies for high–throughput screening, 1997, Current Opinion in Chemical Biology!: 72–78.*
Alla Buzina and Marc J. Shulman: "Infrequent Translation of a Nonsense Codon is Sufficient to Decrease mRNA Level" *Molecular Biology of the Cell 3/99* ; vol. 10, pp. (515–524).
Michael R. Culbertson: "Unforeseen consequences for gene expression, inherited genetic disorder and caner" *TIG 2/99*; vol. 15(2), pp. (74–80).
Howard et. al.: "Aminoglycoside antibodies restore CFTR function by overcoming premature stop mutations" *Nature Medicine4/96*; vol. 2(4), pp. (467–469).
Bedwell et. al.: "Suppression of CFTR premature stop mutation in a bronchial epithelial cell line" *Nature Medicine 11/97*; vol. 3(11) pp. (1280–1284).
Matthias W. Hentze and Andreas E. Kulozik: "A Perfect Message: RNA Surveillance and Nonscence–Mediated Decay" Cell Feb. 5, 1999; vol. 96, pp. (307–310).
Ruiz–Echevarria, et al.: "Making sense of nonscencse in yeast" TIBS11/96; 21, pp. 433–438).
Shulin Li and Miles F. Wilkinson: Nonsencse Surveillance in Lymphocytes638 *Immunity2/98*; vol. 8, pp. 135–141.
Barton–Davis et. al.: "Aminoglycoside antibiotics restore dystrophin function to skelatal muscles of *mdx* mice" *Journal of Clincal Investigation 8/99*; vol. 104(4) pp. (375–381).
Richard J. Jackson and Tim Hunt: "Preparation and Use of Neclease–Treated Rabbit Reticulocyte Lysates for the Translation of Eukaryotic Messenger RNA" *Methods in Enzymology 1983*; vol. 96 pp. (50–75).

\* cited by examiner

Primary Examiner—James Ketter
Assistant Examiner—Richard Schnizer
(74) Attorney, Agent, or Firm—Townsend and Townsend and Crew LLP

(57) ABSTRACT

The present application provides methods of assaying for compounds that inhibit premature translation termination and nonsense mediated RNA decay in cells.

21 Claims, 8 Drawing Sheets

B) RRL REQUIREMENT

METHODS OF ASSAYING FOR COMPOUNDS THAT INHIBIT PREMATURE TRANSLATION TERMINATION AND NONSENSE-MEDIATED RNA DECAY

CROSS-REFERENCES TO RELATED APPLICATIONS

Not applicable.

STATEMENT AS TO RIGHTS TO INVENTIONS MADE UNDER FEDERALLY SPONSORED RESEARCH AND DEVELOPMENT

Not applicable.

BACKGROUND OF THE INVENTION

Chain termination mutations are those in which a base substitution or frameshift mutation changes a sense codon into one of three stop codons (UAA, UAG, or UGA). Studies of yeast, human genetic disorders, and immunoglobulin family gene expression have identified an RNA surveillance mechanism that minimizes the translation and regulates the RNA stability of nonsense RNAs containing such chain termination mutations. This surveillance mechanism is called "nonsense-mediated mRNA decay" ("NMD," see, e.g., Hentze & Kulozik, Cell 96:307–310 (1999); Culbertson, Trends in Genetics 15:74–80 (1999); Li & Wilkinson, Immunity 8:135–141 (1998); and Ruiz-Echevarria et al., TIBS 21-433–438 (1996)). NMD is a post transcriptional mechanism that is operational in both normal cells (i.e., B and T cells) and cells with genetic mutations (i.e., cells with mutations in β-globin, CFTR, and dystrophin).

The NMD machinery discriminates between normal and premature stop codons, and then commits many RNAs with premature stop codons to degradation. In some cases, when the premature stop codon is located near the end of an ORF or in the last exon, the RNA is not subject to NMD and results in production of a truncated polypeptide.

A number of human diseases are caused by nonsense mutations, e.g., p53 associated cancers, retinoblastoma, Duchenne muscular dystrophy, cystic fibrosis, von Willebrand's disease, thalassemias, neurofibromatosis, Tay-Sachs disease, and hemophilia. In cultured cells having premature stop codons in the CFTR gene, synthesis of full length CFTR was observed when the cells were treated with aminoglycosides (see, e.g., Bedwell et al., Nat. Med. 3:1280–1284 (1997); Howard et al., Nat. Med. 2:467–469 (1996)). Furthermore, in a mouse model for Duchenne muscular dystrophy, gentamycin sulfate was found to suppress translational termination at premature stop codons in the dystrophin gene. These antibiotics mediated misreading and insertion of alternative amino acids at the site of the premature stop codon (see, e.g., Barton-Davis et al., J. Clin Invest. 104:375–381 (1999)). Dystrophin produced in this manner provided protection against contraction-induced damage in the mdx mice.

Compounds that suppress premature translation termination would be a useful treatment for numerous diseases caused by nonsense mutations. Accordingly, high throughput assays for drug discovery related to NMD and inhibition of premature translation termination is desirable. This invention provides these assays, as well as other features which will become apparent upon review.

SUMMARY OF THE INVENTION

The present application therefore provides high throughput methods of assaying for compounds that inhibit premature translation termination and nonsense mediated RNA decay in cells.

In one aspect, the present invention provides a method of in vitro screening for compounds that modulate premature translation termination and non-sense-mediated mRNA decay, the method comprising the steps of: (i) incubating a translation assay, the assay comprising an in vitro translation cellular extract; a nucleic acid encoding a polypeptide, wherein the coding sequence for the polypeptide comprises a premature stop codon; and a candidate modulator compound; and (ii) detecting the polypeptide translated from the nucleic acid.

In one embodiment, the cellular extract is from yeast, plants, mammals, or amphibians. In another embodiment, the cellular extract is a eukaryotic reticulocyte lysate, e.g., a rabbit reticulocyte lysate. In another embodiment, the cellular extract is a mammalian tissue culture cell extract, e.g., a HeLa cell S100 extract. In one embodiment, the nucleic acid is an in vitro transcribed RNA.

In another aspect, the present invention provides a method of in vivo screening for compounds that modulate premature translation termination and nonsense-mediated mRNA decay, the method comprising the steps of: (i) expressing in a cell a nucleic acid encoding a polypeptide, wherein the coding sequence for the polypeptide comprises a premature stop codon; (ii) contacting the cell with a candidate modulator compound; and (iii) detecting either the polypeptide translated from the nucleic acid or RNA transcribed from the nucleic acid.

In one embodiment, the nucleic acid comprises a promoter operably linked to a heterologous nucleic acid encoding the polypeptide. In another embodiment, the heterologous nucleic acid encoding the polypeptide comprises an intron and at least two exons comprising coding sequence. In another embodiment, the premature stop codon is located in a last exon. In another embodiment, the heterologous nucleic acid encodes a chimeric polypeptide. In another embodiment, the nucleic acid is an endogenous gene, e.g., an immunoglobulin, α-globin, β-globin, factor VIII, factor IX, vWF, p53, dystrophin, CFTR, Rb, MSH1, MSH2, APC, Wt1, hexosaminidase A, neurofibromin 1, or neurofibromin 2. In another embodiment the cell is adhered to a solid substrate, e.g., a bead, a membrane, and a microtiter plate. In another embodiment, the cell is a human cell or a mouse cell. In another embodiment, the cell is stably transfected with the nucleic acid.

In one embodiment, the nucleic acid encodes an enzyme. In another embodiment, the nucleic acid encodes an immunoglobulin. In another embodiment, the nucleic acid encodes luciferase, green fluorescent protein, red fluorescent protein, phosphatase, peroxidase, kinase, chloramphenicol transferase, or β-galactosidase. In another embodiment, the polypeptide is detected by ELISA, light emission, colorimetric measurements, enzymatic activity, or radioactivity.

In one embodiment, the assay is performed in a well of a microtiter dish, e.g., a microtiter dish having 96 or 384 wells. In another embodiment, the steps of the method are repeated in parallel in a microtiter plate format, wherein between at least about 100 and at least about 6,000 different compounds are tested. In another embodiment, the assay is performed in a high throughput integrated system comprising an automatic pipetting station, a robotic armature, and a robotic controller.

In another aspect, the present invention provides a kit for screening for compounds that modulate translation termination and nonsense-mediated mRNA decay, the kit comprising a nucleic acid encoding a polypeptide, wherein the polypeptide coding sequence comprises a premature stop codon; instructions for practicing a method of screening for compounds that inhibit translation termination at premature stop codons and nonsense mediated RNA decay; and a control compound that inhibits nonsense-mediated RNA decay.

In one embodiment, the control compound is G418 or gentamycin sulfate.

DETAILED DESCRIPTION OF THE INVENTION

Introduction

Figure 1:
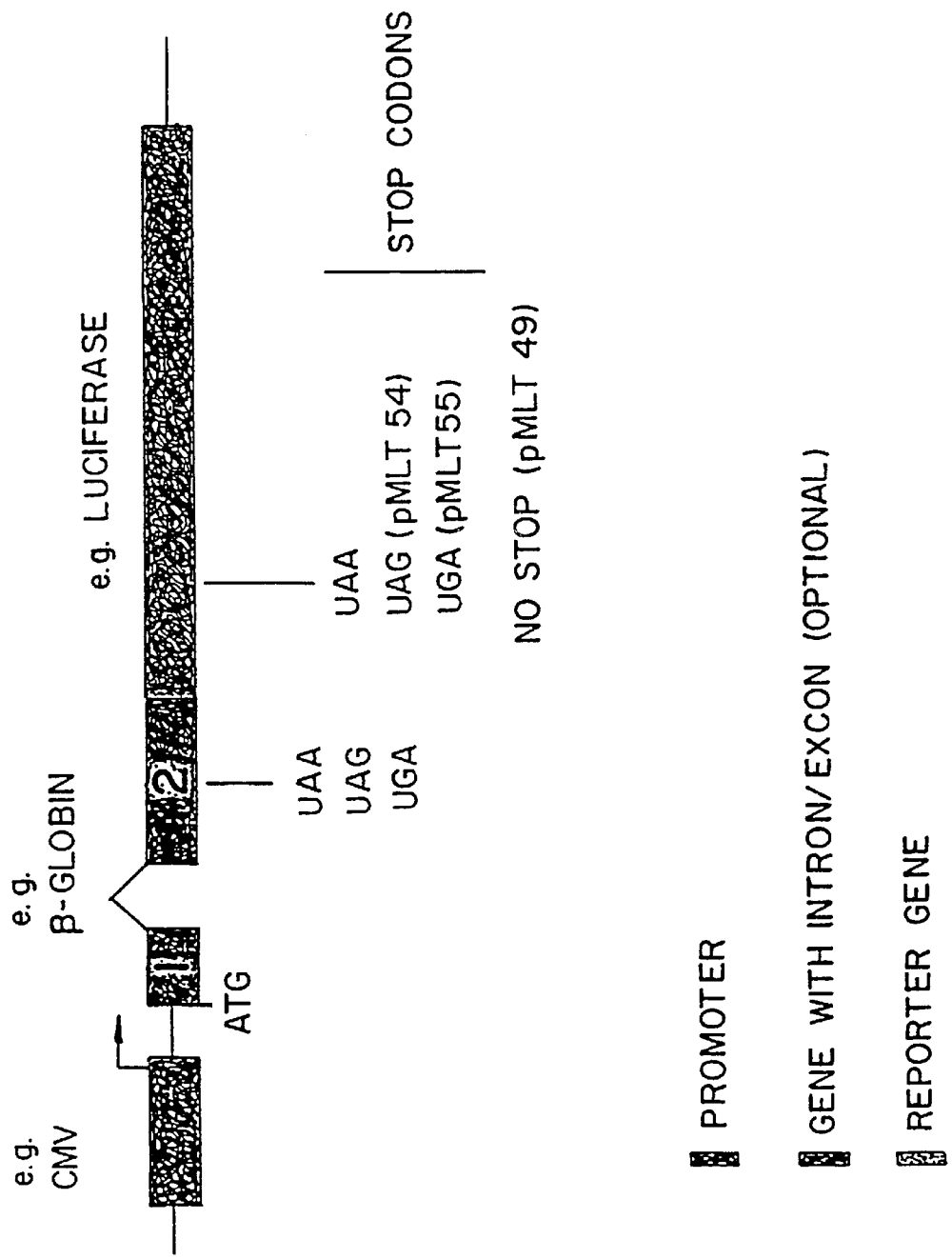
FIG. 1 shows an overview of constructs for assays with transiently or stably transiently infected cells. Positions of stop codons, genes, and promoters are indicated.
Figure 2A:
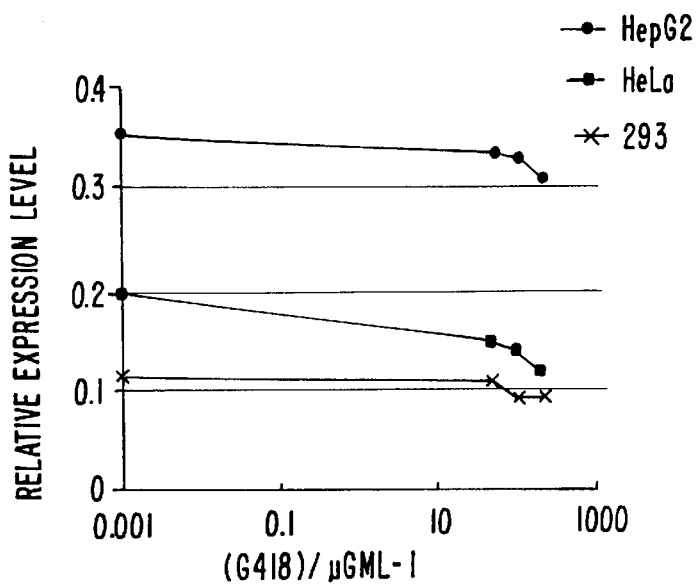
FIGS. 2A–C shows that G418-mediated suppression is not cell line specific. Cells, transiently infected with the indicated plasmids for 24 hours, were exposed to the indicated concentration of G418 (panel A, pMLT49; panel B, pMLT54; panel C, pMLT55). Luciferase activity was measured after a 12 hour exposure.
Figure 2B:
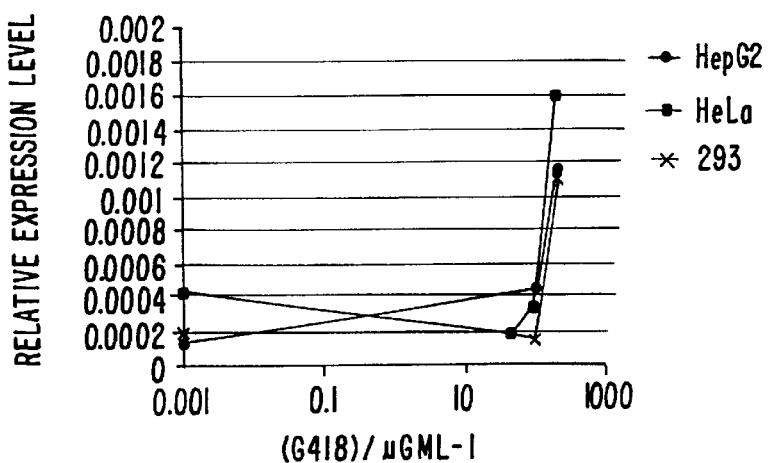
Figure 2C:
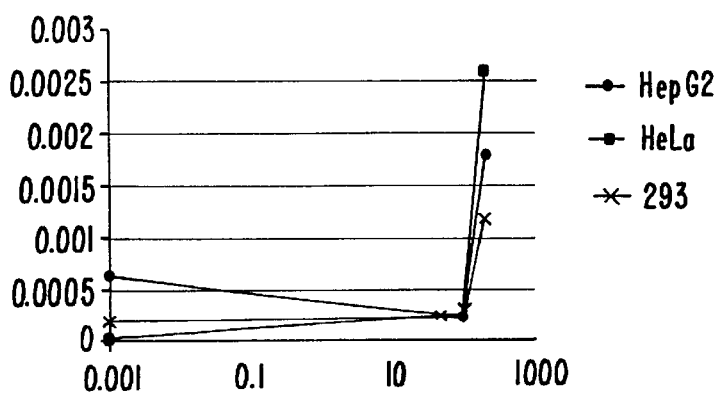

The present invention provides high throughput assay methods for screening compounds that inhibit NMD and premature translation termination caused by nonsense mutations in RNA. The assays can be performed in vitro, using cellular translation extracts or combined transcription-translation extracts and heterologous or endogenous reporter nucleic acids, either DNA or RNA. The assays can also be performed in vivo, using cells with heterologous (transiently or stably transfected) or endogenous reporter nucleic acids. Inhibitory compounds are detected by measuring whether or not full-length reporter RNA or full-length reporter protein produced in the assay.

Inhibitory compounds identified using the assays of the invention are used to treat diseases related to nonsense mutations. The compounds of the invention allow readthrough of the nonsense codons, leading to production of full-length polypeptide. Diseases that are related to nonsense mutations include, e.g., blood diseases, e.g., thalassemia (α-globin and β-globin genes), hemophilia A and B (factor VIII and factor IX genes), and von Willebrand's disease (vWF gene); p53 related cancers, e.g. lung, breast, colon, pancreatic, esophageal, non-Hodgkin's lymphoma, and ovarian cancer (p53 gene); colorectal cancers (APC, MSH1, and MSH2 genes); cystic fibrosis (CFTR gene); Duchenne muscular dystrophy; (dystrophin gene) Tay-Sachs disease (hexosaminidase A gene); Wilms tumor (Wt1 gene); retinoblastoma (Rb gene), neurofibromatosis (NF1 and NF2 genes); kidney stones, and collagen disorders.

As described above, in one embodiment, the assay is an in vitro assay. The in vitro assay uses a translation extract or a transcription-translation extract and a reporter nucleic acid molecule encoding a reporter polypeptide with a premature stop codon to test compounds that are potential inhibitors of nonsense-mediated mRNA decay and premature translation termination. Inhibitory compounds are identified by detecting production of a full length polypeptide translated from the nucleic acid molecule.

The reporter nucleic acid encodes any polypeptide, where the full length polypeptide can be labeled or detected by any of the methods described herein. In one embodiment, the polypeptide is an enzyme such as luciferase, phosphatase, e.g., alkaline phosphatase, peroxidase, e.g., horseradish peroxidase, kinase, chloramphenicol transferase, or β-galactosidase. In another embodiment, the polypeptide is green fluorescent protein or red fluorescent protein. In another embodiment, the polypeptide is any polypeptide detectable with an antibody, or by radioactive labeling, etc. The stop codon can be at any position in the polypeptide that is N-terminal with respect to the correct stop codon for the full-length polypeptide.

The in vitro reaction can be a translation reaction, or a combined transcription-translation reaction. Cellular extracts for translation and transcription-translation are commercially available or can be prepared using standard methods known to those of skill in the art (see, e.g., Sambrook et al., *Molecular Cloning, A Laboratory Manual* (2nd ed. 1989); Kriegler, *Gene Transfer and Expression: A Laboratory Manual* (1990); *Current Protocols in Molecular Biology* (Ausubel et al., eds., 1994); and Jackson & Hunt, *Methods in Enzymology* 96:50–75 (1983)). For a combined transcription-translation reaction, the nucleic acid is typically a DNA molecule that is transcribed into RNA, which is then translated. For a translation reaction, the nucleic acid is typically an RNA, either an in vitro transcribed RNA or an endogenous RNA. Methods of making in vitro transcribed RNA are well know in the art, e.g., by using bacterial RNA polymerases such as SP6 and T7 (see, e.g., Contreras et al., *Nuc. Acids Res.* 10:6353 (1982)). Suitable cellular extracts for the translation or transcription-translation reaction include those from yeast, fission yeast, plants, amphibians (e.g., Xenopus), plants (e.g., wheat germ) and mammals (see, e.g., Krieg & Melton, *Nature* 308:203 (1984); Dignam et al., *Methods Enzymol.* 182:194–203 (1990)). In one embodiment, the extract is a reticulocyte lysate, preferably from rabbits. In another embodiment, the extract is from cultured cells, preferably mouse, rat, or human cells, e.g., an S100 extract from HeLa cells (Dignam et al., *Nuc. Acids Res.* 11:1475–1489 (1983)).

In another embodiment, the assay is an in vivo, cell based assay. The in vivo assay uses a cell, typically a cultured cell, and a reporter nucleic acid molecule encoding a reporter polypeptide with a premature stop codon to test compounds that are potential inhibitors of nonsense-mediated mRNA decay and premature translation termination. Inhibitory compounds are identified by detecting production of a full length reporter polypeptide translated from the nucleic acid molecule, or by detecting full length reporter RNA transcribed from the reporter nucleic acid.

The reporter nucleic acid encodes any polypeptide, where the full length polypeptide can be labeled or detected by any of the methods described herein. The reporter nucleic acid can be an endogenous gene or a heterologous gene that is stably or transiently expressed in the cell. In addition, a heterologous reporter nucleic acid can encode a chimeric polypeptide, e.g., a chimera of different polypeptides and/or different polypeptides from different species, for example, a chimera comprising an exon and an intron from human β-globin and a sequence encoding fly luciferase. In one embodiment, the reporter nucleic acid is a heterologous nucleic acid encoding an enzyme such as luciferase, phosphatase, e.g., alkaline phosphatase, peroxidase, e.g., horseradish peroxidase, kinase, chloramphenicol transferase, or β-galactosidase. In another embodiment, the heterologous nucleic acid encodes green fluorescent protein, red fluorescent protein, or an immunoglobulin or a fragment thereof. In another embodiment, the reporter nucleic acid is an endogenous gene, e.g., an immunoglobulin gene, α-globin, β-globin, factor VIII, factor IX, vWF, p53, dystrophin, CFTR, Rb, MSH1, MSH2, APC, Wt1, hexosaminidase A, neurofibromin 1, or neurofibromin 2. In another embodiment, the polypeptide is any polypeptide detectable with an antibody, or by radioactive labeling, etc.

The premature stop codon can be at any position in the polypeptide that is N-terminal with respect to the correct stop codon for the full-length polypeptide. The reporter polypeptide can include introns, with the premature stop codon positioned in any one of the exons. The premature stop codon can be naturally occurring, or can be produced by in vitro mutagenesis techniques such as PCR, linker insertion, oligonucleotide mediated mutagenesis, and random chemical mutagenesis, both in vivo and in vitro.

Any suitable eukaryotic cultured cell can be used in the methods of the invention, e.g., insect cells, yeast cells, and mammalian cells, preferably human cells. The cells can be transformed cell lines or primary cells, and can either be adherent or in suspension. In one embodiment the cell is a hybridoma or a pre-B cell or a cancer cell. In another embodiment, the cell is a 293 cell, a HeLa cell, a HepG2 cell, a K562 cell, or a 3T3 cell. The cell can either be in solution or can be anchored to a solid substrate such as a bead or a plate.

Preferably, the in vitro or in vivo assay is performed in a high throughput format, using microtiter plates and liquid robotic handling, or cell sorting using fluorescent antibodies or ligands (FACS). The in vitro and in vivo assays can be incubated with the test compound for any suitable length of time, i.e., from about 15, 30, or 45 minutes up to an hour, one hour, one and a half hours, two hours, four hours, six hours, twelve hours or more up to a day or more for an in vitro reaction, and from one hour, two hours, four hours, six hours, twelve hours, or more, up to a day, two days, three days or more for an in vivo reaction. The time period of incubation of the test compound and the reporter reaction can be determined by one of skill in the art using standard methodology.

Definitions

As used herein, the following terms have the meanings ascribed to them unless specified otherwise.

By "detecting either the polypeptide translated from the nucleic acid or RNA transcribed from the nucleic acid" is meant assays for a compound that increases or decreases a parameter that is indirectly or directly under the influence of premature translation termination and/or NMD, e.g., functional, physical and chemical effects. Such effects can be measured by any means known to those skilled in the art, e.g., changes in spectroscopic characteristics (e.g., fluorescence, absorbance, refractive index), enzyme activity, protein expression, voltage-sensitive dyes, radioisotope efflux, inducible markers, levels of RNA expression, proper splicing of an mRNA, ligand binding assays, changes in intracellular second messengers such as cAMP, cGMP, and inositol triphosphate (IP3), changes in intracellular calcium levels, and the like.

"Inhibitors" "suppressors" and "modulators" of are used interchangeably to refer to inhibiting, suppressing, or modulating premature translation termination and NMD with compounds identified using in vitro and in vivo assays. Inhibitors are compounds that, e.g., bind to, partially or totally block, decrease, prevent, delay, inactivate, desensitize, or down regulate premature translation termination and NMD. Modulators include naturally occurring and synthetic ligands, antagonists, agonists, small chemical molecules and the like. Such assays for inhibitors include, e.g., expressing a test nucleic acid in an in vitro assay or in a cell, applying putative modulator compounds, and then determining the functional effects on RNA or protein levels of the test nucleic acid. Samples or assays that are treated with a potential inhibitor or modulator are compared to control samples without the inhibitor or modulator to examine the extent of inhibition. Control samples (untreated with inhibitors) are assigned a relative activity value of 100%. Inhibition of premature translation termination and NMD is achieved when the activity value relative to the control is at least 110%, optionally 150%, 200%, 500%, 100%, 200%, 5000%, 10,000% or higher, i.e., 1½ fold, 2 fold, 3 fold, 4 fold, 5 fold, 10 fold or more increase in activity. Inhibition can be measured by detecting either full length polypeptide or full length RNA. Optionally, an inhibitory control reaction is included, using a known inhibitor such as an aminoglycoside antibiotic, e.g., G418.

"Antibody" or "immunoglobulin" are used interchangeably and refer to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the various immunoglobulin diversity/joining/variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$–$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990)).

For preparation of monoclonal or polyclonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552–554 (1990); Marks et al., *Biotechnology* 10:779–783 (1992)).

A "chimeric antibody" or "chimeric immunoglobulin" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiralmethyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-ITUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, *Proteins* (1984)).

A "label" or a "detectable moiety" is a composition detectable by spectroscopic, photochemical, biochemical, immunochemical, or chemical means. For example, useful labels include $^{32}p$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element or a initiator element. A promoter also optionally includes nearby activator or repressor binding site(s) (e.g., SP1 or NF kappa B sites), or distal enhancer or repressor elements, which can be located as much as several thousand base pairs from the start site of transcription. A "constitutive" promoter is a promoter that is active under most environmental and developmental conditions. An "inducible" promoter or a "tissue specific" promoter is a non-constitutive promoter that is active under, e.g., environmental, temporal, tissue specific, or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

Cloning and Expression of Reporter Genes

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)). Standard mutagenesis methods can be used to introduce nonsense mutations into the reporter genes or endogenous genes of choice.

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

B. Cloning Methods for the Isolation of Nucleotide Sequences

In general, the nucleic acid sequences encoding heterologous reporter genes of the invention are isolated from cDNA and genomic DNA libraries by hybridization with probes, or isolated using amplification techniques with oligonucleotide primers. For example, reporter sequences are typically isolated from mammalian nucleic acid (genomic or cDNA) libraries by hybridizing with a nucleic acid probe, the sequence of which can be derived from Genebank or other database or publication, or by using a cloned ortholog. A suitable tissue from which RNA and cDNA is isolated is determined by one of skill in the art. Methods for making and screening genomic and cDNA libraries are well known (see, e.g., Gubler & Hoffman, *Gene* 25:263–269 (1983); Sambrook et al., supra; Ausubel et al., supra). Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.*, 72:3961–3965 (1975).

Amplification techniques such as PCR and LCR using primers can also be used to amplify and isolate reporter sequences from DNA or RNA (see, e.g., Dieffenfach & Dveksler, *PCR Primer: A Laboratory Manual* (1995); U.S. Pat. Nos. 4,683,195 and 4,683,202; *PCR Protocols: A Guide to Methods and Applications* (Innis et al., eds, 1990)). These primers can be used, e.g., to amplify either the full length sequence or a probe of one to several hundred nucleotides, which is then used to screen a mammalian library for full-length clones. In addition, degenerate primers encoding the following amino acid sequences can be used to amplify a sequence of a particular reporter gene. As described above, such primers can be used to isolate a full length sequence, or a probe which can then be used to isolated a full length sequence, e.g., from a library. Nucleic acids encoding a reporter gene can also be isolated from expression libraries using antibodies as probes.

Synthetic oligonucleotides can be used to construct recombinant reporter genes. This method is performed using a series of overlapping oligonucleotides usually 40–120 bp in length, representing both the sense and nonsense strands of the gene. These DNA fragments are then annealed, ligated and cloned.

Optionally, nucleic acids encoding chimeric proteins comprising an reporter gene, e.g., a combination of luciferase and β-globin can be made according to standard techniques. The chimeric genes can also be combinations of genes or exons from different species, e.g., bacteria (e.g., *E. coli*), yeast, invertebrates such as flies and nematodes, and mammalian genes (e.g., rat, mouse, or human genes). Often the chimeric gene has an exon and an intron from one gene, and a second exon from another gene. Other heterologous proteins of choice for the production of chimeric genes include, e.g., red or green fluorescent protein, a phosphatase, a peroxidase, a kinase, chloramphenicol transferase, luciferase, β-galactosidase, a glutamate receptor, and the rhodopsin presequence, .

C. Expression in Prokaryotes and Eukaryotes

To obtain expression of a cloned gene or nucleic acid one typically subclones the sequence into an expression vector that contains a promoter to direct transcription, optionally a transcription or translation terminator, and optionally for a nucleic acid encoding a protein, a ribosome binding site for translational initiation. Suitable bacterial promoters are well known in the art and described, e.g., in Sambrook et al. and Ausubel et al. Bacterial expression systems are available in, e.g., *E. coli*, Bacillus sp., and Salmonella (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available. RNA expression systems such as those using SP6, T3 or T7 RNA polymerase are also well known to those in the art and are commercially available.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the nucleic acid in host cells. A typical expression cassette thus contains a promoter operably linked to the nucleic acid sequence and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

The elements that are typically included in expression vectors also include a replicon that functions in *E. coli,* a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

Standard transfection methods are used to produce bacterial, mammalian, yeast or insect cell lines that express the nucleic acid. Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell.

After the expression vector is introduced into the cells, the transfected cells are cultured under conditions favoring expression of the reporter gene, using standard techniques identified below.

In addition to heterologous reporter genes, endogenous genes can also be used as reporters. Cells comprising suitable endogenous genes such as CFTR, dystrophin, immunoglobulins, β-globin, p53, retinoblastoma, neurofibromin, etc. are cultured under conditions favoring expression of the endogenous reporter gene, using standard techniques described below.

Cell Culture and Selection

The culture of cells used in the assays of the present invention, including cell lines and cultured cells from tissue or blood samples is well known in the art. Freshney (*Culture of Animal Cells, a Manual of Basic Technique* ($3^{rd}$ ed. 1994)) and the references cited therein provides a general guide to the culture of cells. Additional information on cell culture is found in Ausubel and Sambrook, supra. Cell culture media are described in *The Handbook of Microbiological Media* (Atlas & Parks, eds., 1993). Additional information is found in commercial literature such as the *Life Science Research Cell Culture Catalogue* (1998) from Sigma-Aldrich, Inc (St Louis, Mo.) and, e.g., the *Plant Culture Catalogue and Supplement* (1997) also from Sigma-Aldrich, Inc (St Louis, Mo.). Cells can be grown in bulk flasks and added to the substrate (e.g., microtiter plate) or can be grown directly on the substrate (e.g., in the wells of the microtiter plate, depending on the intended application and available equipment.

Selection of cells is based upon the intended application. Where inhibition of premature translation termination of a gene in a particular cell is a target of the assay, the particular cell, or a related cell culture form of the cell is typically the target. In some embodiments, adherent cells which will adhere during culture to the substrate of the container in which the cells are placed are preferred. Many examples of adherent cell types are known, including epithelial and endothelial cell types. Cells which are not naturally adherent can often be made adherent by chemically modifying the substrate (e.g., treating the substrate with silane to provide OH groups, or with amine reagents to provide amine groups) or by expressing cell surface receptor molecules on the cell (e.g., recombinantly) and providing an appropriate ligand fixed on the substrate. In one embodiment, the cell is a hybridoma or a pre-B cell. In another embodiment, the cell is a mammalian or mouse cell, e.g., a 293 cell, a HeLa cell, a HepG2 cell, a K562 cell, or a 3T3 cell.

Inhibitors and High Throughput Techniques

A. Inhibitors

The compounds tested as inhibitors and modulators of premature translation termination and NMD can be any small chemical compound, or a biological entity, such as a protein, sugar, nucleic acid or lipid. Typically, test compounds will be small chemical molecules and peptides. Essentially any chemical compound can be used as a potential modulator in the assays of the invention. The compounds can be dissolved in aqueous or organic solutions (e.g., methanol, DMSO, or a mixture of organic solvents). The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. *J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274:1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

B. Solid State and Soluble High Throughput Assays

In one embodiment the invention provides in vitro soluble assays in a high throughput format. In another embodiment, the invention provides soluble or solid phase based in vivo assays in a high throughput format, where the cell or tissue is attached to a solid phase substrate. Optionally, the in vitro assay is a solid phase assay.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100- about 1500 different compounds. It is possible to assay several different plates per day; assay screens for up to about 6,000–20,000 different compounds is possible using the integrated systems of the invention. More recently, microfluidic approaches to reagent manipulation have been developed.

The molecule or cell of interest can be bound to the solid state component, directly or indirectly, via covalent or non covalent linkage of a tag and or a tag binder. A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Alabama. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:6031–6040 (1988) (describing synthesis of various peptide sequences on cellulose disks); Fodor et al., *Science*, 251:767–777 (1991); Sheldon et al., *Clinical Chemistry* 39(4):718–719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Labels and Means of Detection

Detectable labels and moieties can be primary labels (where the label comprises an element which is detected directly or which produces a directly detectable element) or secondary labels (where the detected label binds to a primary label, e.g., as is common in immunological labeling). An introduction to labels, labeling procedures and detection of labels is found in Polak & Van Noorden (1997) *Introduction to Immunocytochemistry* ($2^{nd}$ ed. 1977) and *Handbook of Fluorescent Probes and Research Chemicals,* a combined handbook and catalogue Published by Molecular Probes, Inc., Eugene, Oreg. Primary and secondary labels can include undetected elements as well as detected elements.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means.

Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horseradish peroxidase, alkaline phosphatase etc.), spectral colorimetric labels such as colloidal gold or colored glass or plastic (e.g. polystyrene, polypropylene, latex, etc.) beads.

The label may be coupled directly or indirectly to a component of the detection assay according to methods well known in the art. Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. As indicated above, a wide variety of labels may be used, with the choice of label depending on sensitivity required, ease of conjugation with the compound, stability requirements, available instrumentation, and disposal provisions.

In general, a detector which monitors a particular probe or probe combination is used to detect the recognition reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling nucleic acids is digitized for subsequent computer analysis.

Preferred labels include those which utilize enzymes such as hydrolases, particularly phosphatases, kinases, esterases and glycosidases, or oxidotases, particularly peroxidases; chemiluminescence (e.g., enzymes such as horseradish peroxidase or alkaline phosphatase with substrates that produce photons as breakdown products; kits available, e.g., from Molecular Probes, Amersham, Boehringer-Mannheim, and Life Technologies/ Gibco BRL); color production (using, e.g., horseradish peroxidase, β-galactosidase, or alkaline phosphatase with substrates that produce a colored precipitate; kits available from Life Technologies/Gibco BRL, and Boehringer-Mannheim); hemifluorescence (using, e.g., alkaline phosphatase and the substrate AttoPhos (Amersham) or other substrates that produce fluorescent products); fluorescence (e.g., using Cy-5 (Amersham), fluorescein, and other fluorescent tags, and fluorescent proteins such as Green and Red Fluorescent Protein); antibodies bound to a detectable moiety, and radioactivity. Other methods for labeling and detection will be readily apparent to one skilled in the art. For example, phenotypic changes such as drug resistance can be used as a "label" in the present invention.

One preferred example of detectable secondary labeling strategies utilizes an labeled antibody which recognizes a cell surface molecule such as an immunoglobulin or a channel molecule such as CFTR. The antibody is detected using FACS. In another embodiment, an antibody is used in an ELISA assay to detect a reporter molecule of the invention.

Preferred enzymes that can be used as reporters or detectable moieties include, e.g., β-galactosidase, luciferase, green or red fluorescent protein, kinase, peroxidase, e.g., horse radish peroxidase, phosphatase, e.g., alkaline phosphatase, and chloramphenicol transferase. The chemiluminescent substrate for luciferase is luciferin. One embodiment of a chemiluminescent substrate for β-galactosidase is 4-methylumbelliferyl-β-D-galactoside. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-dioxetane-3,2'-adamantane], which is detected with a luminometer. Embodiments of horse radish peroxidase substrates include 2,2' azino-bis(3-ethylbenzthiazoline-6 sulfonic acid) (ABTS), 5-aminosalicylic acid (5AS), o-dianisidine, and o-phenylenediamine (OPD), which are detected with a spectrophotometer; and 3,3,5,5'-tetramethylbenzidine (TMB), 3,3' diaminobenzidine (DAB), 3-amino-9-ethylcarbazole (AEC), and 4-chloro-1-naphthol (4C1N), which are detected visually. Other suitable substrates are known to those skilled in the art. The enzyme-substrate reaction and product detection are performed according to standard procedures known to those skilled in the art and kits for performing enzyme immunoassays are available as described above.

In one embodiment, inhibition of premature translation termination or NMD is measured by quantitating the amount of label in a cell fixed to a solid support. Typically, presence of a test compound during cell incubation will increase or decrease the amount of label relative to a control incubation which does not comprise the test compound, or as compared to a baseline established for a cell type and culture condition (e.g., with a reporter molecule). Means of detecting and quantitating labels are well known to those of skill in the art. Thus, for example, where the label is a radioactive label, means for detection include a scintillation counter or photographic film as in autoradiography. Where the label is optically detectable, typical detectors include microscopes, cameras, phototubes and photodiodes and many other detection systems which are widely available.

RNA expression can also analyzed by techniques known in the art, e.g., reverse transcription and amplification of mRNA, e.g., RTQ-PCR, isolation of total RNA or poly $A^+$ RNA, northern blotting, dot blotting, in situ hybridization, RNase protection, probing DNA microchip arrays, and the like. In one embodiment, high density oligonucleotide analysis technology (e.g., GeneChip™) is used to identify reporter RNA molecules of the invention, see, e.g., Gunthand et al., *AIDS Res. Hum. Retroviruses* 14: 869–876 (1998); Kozal et al., *Nat. Med.* 2:753–759 (1996); Matson et al., *Anal. Biochem.* 224:110–106 (1995); Lockhart et al., *Nat. Biotechnol.* 14:1675–1680 (1996); Gingeras et al., *Genome Res.* 8:435–448 (1998); Hacia et al., *Nucleic Acids Res.* 26:3865–3866 (1998).

Kits

The present invention also provides for kits for screening for inhibitors of premature translation termination and NMD. Such kits can be prepared from readily available materials and reagents. For example, such kits can comprise any one or more of the following materials: in vitro translation cellular extract; a nucleic acid encoding a polypeptide, wherein the coding sequence for the polypeptide comprises a premature stop codon, reaction tubes, and instructions for testing inhibitor activity. A wide variety of kits and components can be prepared according to the present invention, depending upon the intended user of the kit and the particular needs of the user.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example I

Cell-based Assay

On day 1, clone 55-31, a 293 cell line stably transfected with pMLT 55 (see FIG. 1) was plated in 96 well plates in the morning in DMEM media with 10% fetal bovine serum. Approximately 80 plates are plated at 40,000 cells per well in 100 μL. The cells were incubated overnight at 37° C.

On day two, test compounds (1 μL of 1 mM stock solution in 100 μL DMSO; 10 μM final concentration) were added. G418-(1 mg/ml) was added to column 12 of each plate as a control. The plates were incubated at 37° C. for 12–16 hours.

Figure 3A:
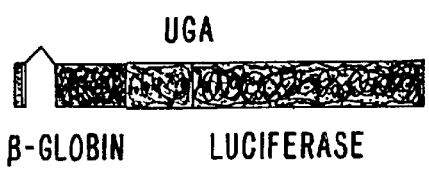
FIGS. 3A–B shows G418-mediated suppression in various clones of stably transfected 293 cells with plasmid pMLT55 (panel A, relative luciferase activity; panel B, fold activation). The indicated independent clones were exposed to the indicated concentrations of G418. Luciferase activity was measured after a 12 hour exposure.
Figure 3A:
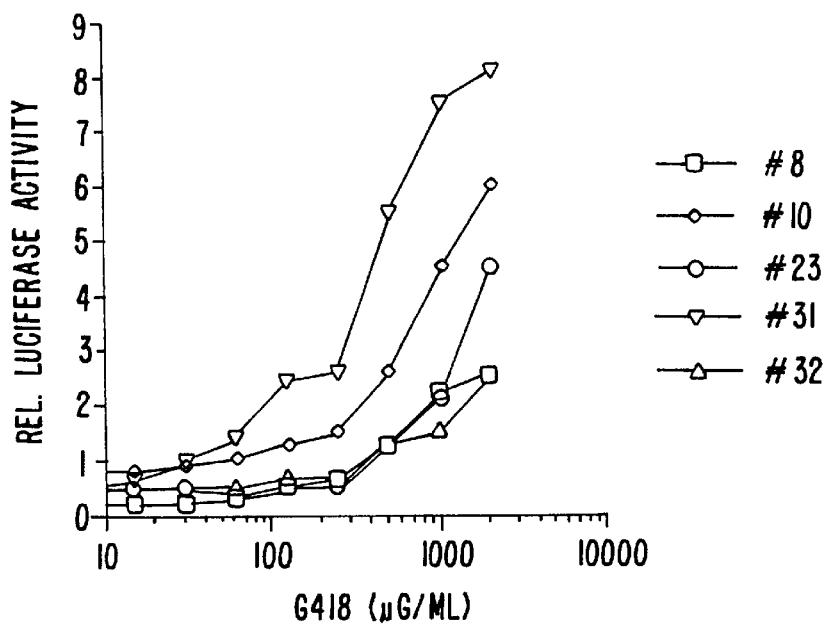
Figure 3B:
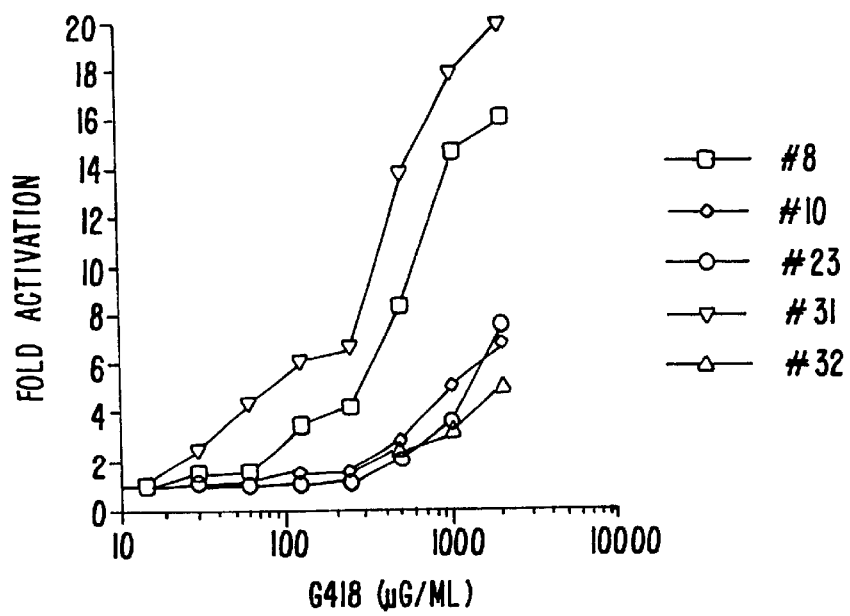
Figure 4:
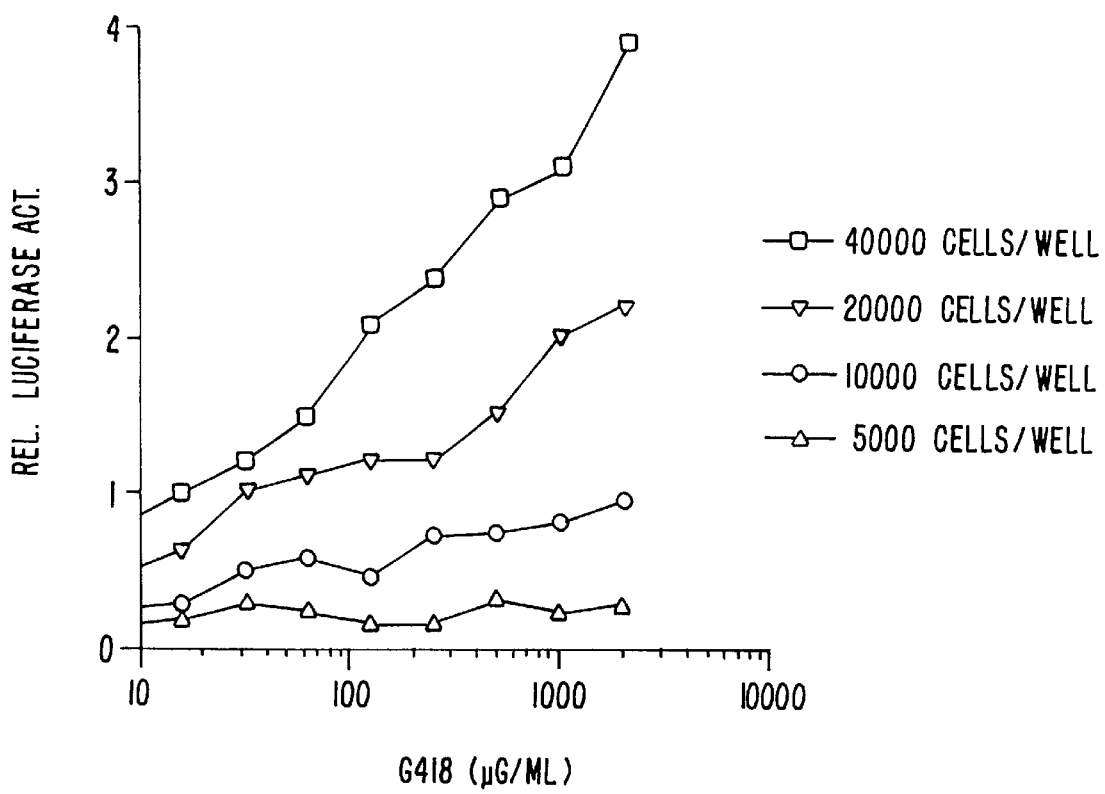
FIG. 4 shows G418-mediated suppression in a stably transfected 293 cell line (clone #31) in high throughput format (96 well plate). The indicated cell numbers were plated per well of a 96 well plate. Cells were exposed to the indicated concentrations of G418. Luciferase activity was measured after a 12 hour exposure on a robotic 96 well plate reader. Gentamycin was also used to inhibit NMD and premature translation termination.

On day three, luciferase substrate was added to the cells and the plates were read on a Torcon automated luciferase assay reader for 96 well plates (see, e.g., FIGS. 3–4). Luciferase substrate is commercially available, e.g., from Promega.

Optionally, days one and two can be combined, with plating early in the day and compounds added late in the day, with overnight incubation and then assaying for luciferase activity on the following day.

Example II

Biochemical Assay

Figure 5:
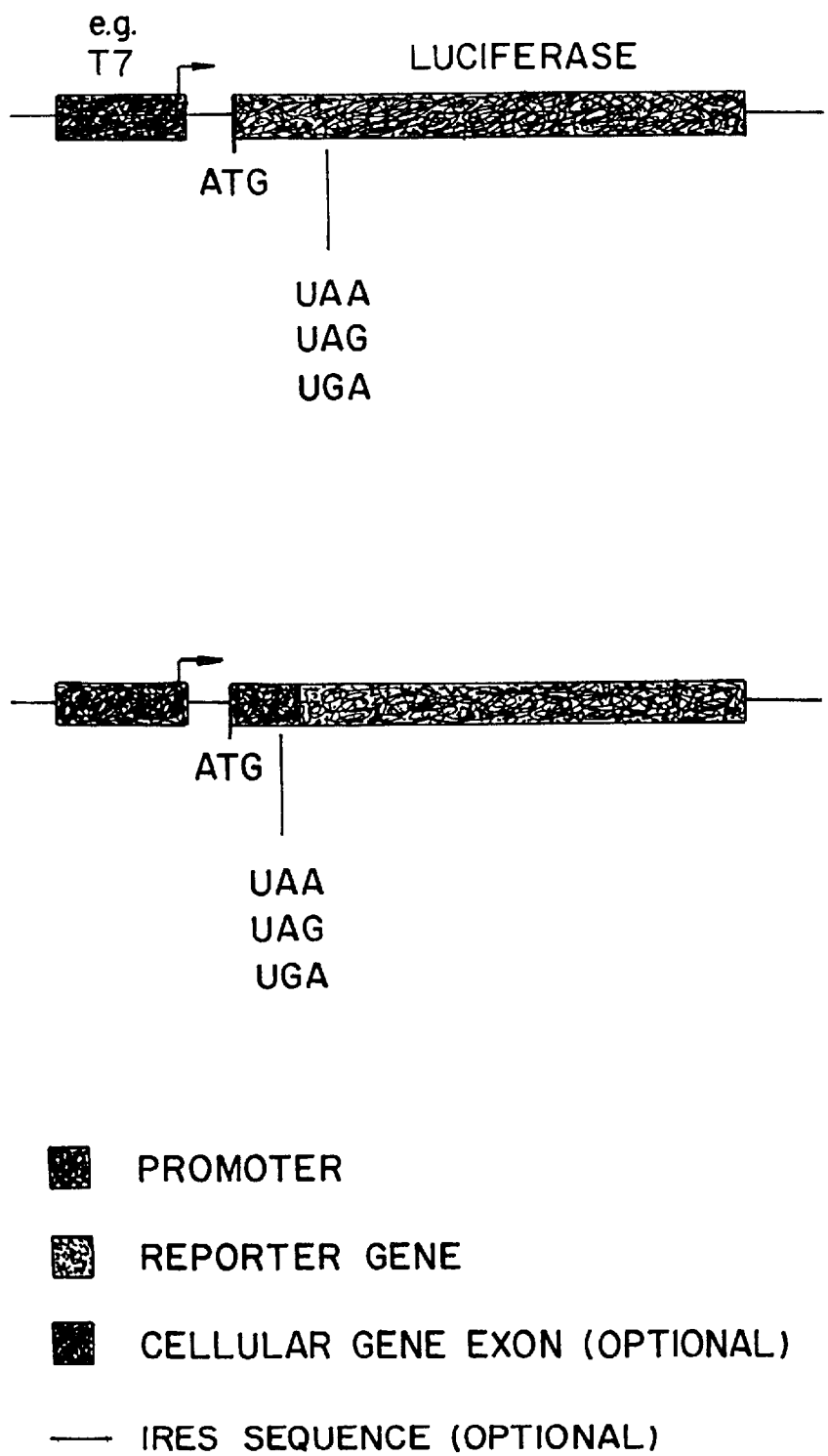
FIG. 5 shows an overview of constructs for use in a biochemical suppression assay using RRL (rabbit reticulocyte lysate). Positions of stop codons, genes, IRES sequence, and promoter regions are indicated.
Figure 6C:
FIGS. 6A–D shows properties of the biochemical suppression assay using RRL. In vitro translation reactions were performed in the presence of the indicated amounts of RRL and luciferase RNA (panels A and B, wild type; panels C and D, stop codon). Low levels of luciferase activity is RNA (panels A and C) and RRL (panels B and D) dependent. WT and stop codon-containing luciferase RNA are schematically shown. Luciferase activity was measured after 90 minutes of incubation. Reactions were performed in a 96 well format.
Figure 6C:
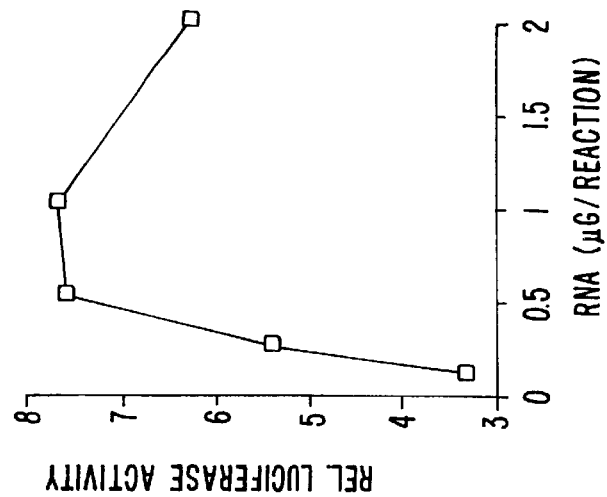
Figure 6A:
Figure 6A:
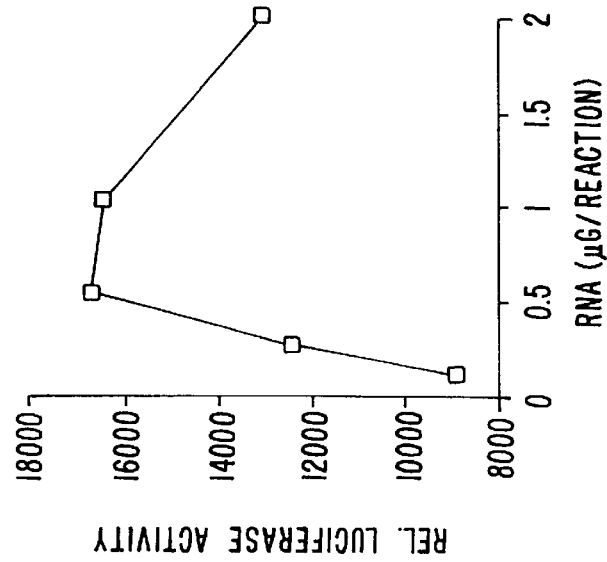
Figure 6D:
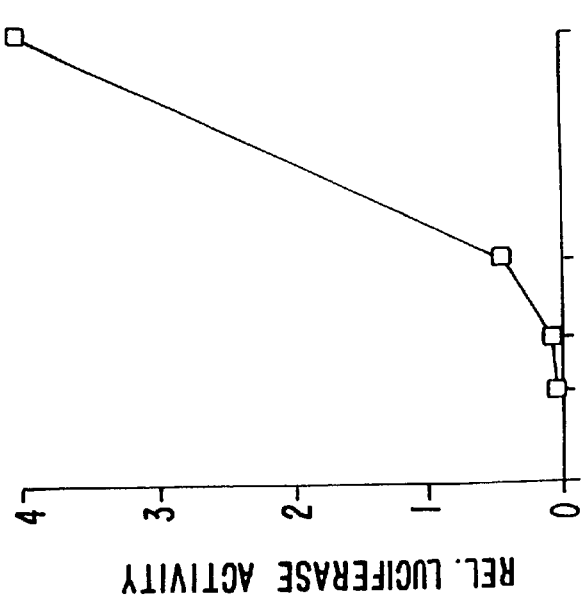
Figure 6B:
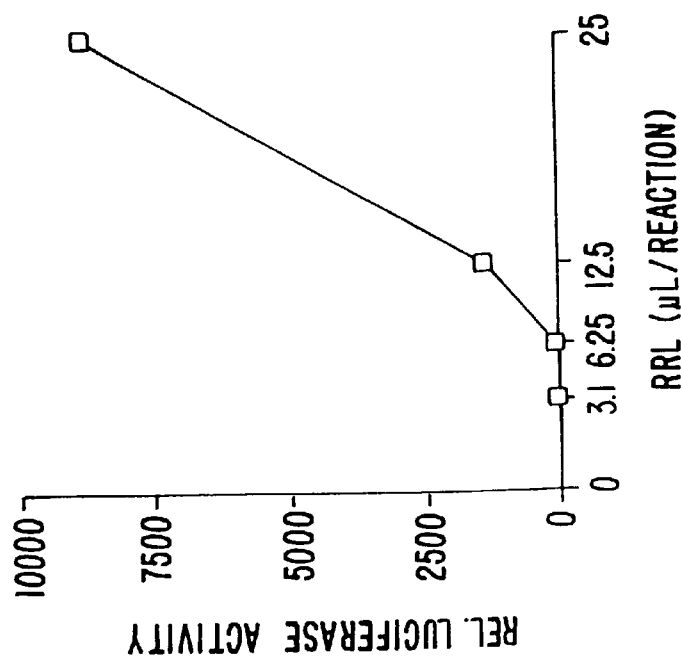
Figure 7B:
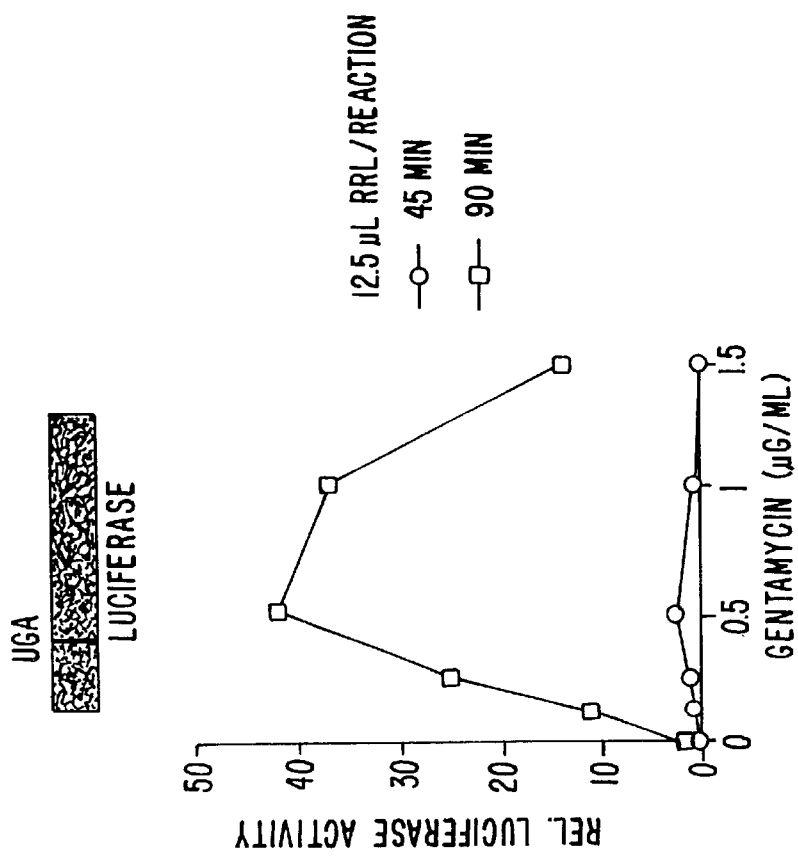
FIGS. 7A–B shows that suppression by gentamycin is time dependent. In vitro translation assays were performed in the presence of RRL, luciferase RNA (panel A, WT; panel B, stop codon) and the indicated concentrations of gentamycin. Reactions were incubated 45 or 90 minutes before luciferase activity was determined. WT and stop codon containing RNA are schematically shown. The reactions were performed in either a 96 or 384 well format.
Figure 7A:
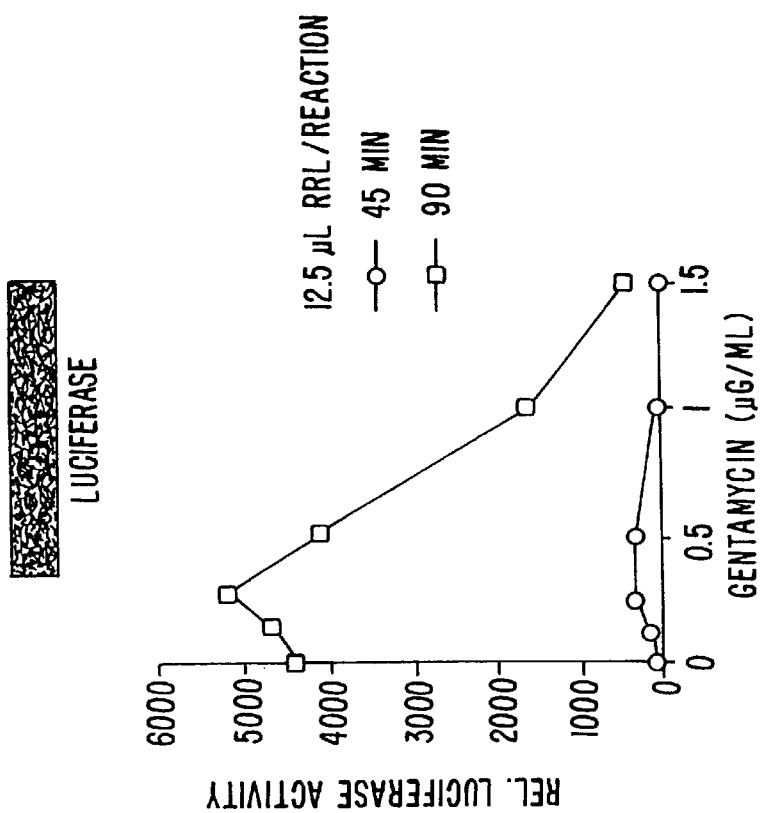

In vitro synthesized reporter RNA (see constructs in FIG. 5) was added to 15 μL of filly supplemented rabbit reticulocyte lysate according to standard methodology (prepared by the method of Jackson & Hunt, *Methods in Enzymology* 96:50–75 (1983). 0.5 to 1 μg of in vitro transcribed RNA was used per reaction. The reaction was mixed with 15 μL of a 2% DMSO solution containing 20 μM of test compound. The reaction was incubated for 90 minutes at 30° C. in a humidified incubator. Luciferase substrate was added and luciferase activity was read on a Torcon automated reader (see FIGS. 6–7).

What is claimed is:

1. A method of screening for compounds that inhibit premature translation termination thereby increasing the amount of full-length polypeptide, the method comprising the steps of:
   (i) expressing in a culture cell a nucleic acid encoding a chimeric polypeptide, wherein the coding sequence for the polypeptide comprises a premature stop codon and the nucleic acid comprises a promoter operably linked to a heterologous nucleic acid encoding the chimeric polypeptide, which heterologous nucleic acid comprises an intron and at least two exons comprising coding sequence;
   (ii) contacting the cell with a candidate compound; and
   (iii) detecting an increase in the amount of the full-length polypeptide encoded by nucleic acid.

2. The method of claim 1, wherein the premature stop codon is located in a last exon.

3. The method of claim 1, wherein the heterologous nucleic acid encodes a chimeric polypeptide comprising luciferase-encoding and β-globin-encoding nucleic acids.

4. The method of claim 1, wherein the heterologous nucleic acid encodes an enzyme.

5. The method of claim 1, wherein the heterologous nucleic acid encodes luciferase, green fluorescent protein, red fluorescent protein, phosphatase, peroxidase, kinase, chloramphenicol transferase, or β-galactosidase.

6. The method of claim 1, wherein the heterologous nucleic acid encodes an immunoglobulin.

7. The method of claim 1, wherein the heterologous nucleic acid comprises a nucleic acid sequence encoding a α-globin, β-globin, factor VIII, factor IX, vWF, p53, dystrophin, CFTR, Rb, MSH1, MSH2, APC, Wt1, hexosaminidase A, neurofibromin 1, or neurofibromin 2.

8. The method of claim 1, wherein the polypeptide is detected by ELISA, light emission, colorimetric measurements, enzymatic activity, drug resistance, FACS, or radioactivity.

9. The method of claim 1, wherein the assay is performed in a well of a microtiter dish.

10. The method of claim 1, wherein the microtiter dish has 96 or 384 wells.

11. The method of claim 9, further comprising repeating steps (i)–(iii) in parallel in a microtiter plate format, wherein between at least about 100 and at least about 6,000 different compounds are tested.

12. The method of claim 1, wherein the assay is performed in a high throughput integrated system comprising an automatic pipetting station, a robotic armature, and a robotic controller.

13. The method of claim 1, wherein the cell is adhered to a solid substrate.

14. The method of claim 13, wherein the solid support is selected from the group consisting of a bead, a membrane, and a microtiter plate.

15. The method of claim 11, wherein the cell is a human cell or a mouse cell.

16. The method of claim 1, wherein the cell is stably transfected with the nucleic acid.

17. A kit for screening for compounds that inhibit translation termination and nonsense-mediated mRNA decay, the kit comprising a nucleic acid encoding a chimeric polypeptide, wherein the polypeptide coding sequence comprises a premature stop codon, and the nucleic acid comprises a promoter operably linked to a heterologous nucleic acid encoding the chimeric polypeptide, which heterologous nucleic acid comprises an intron and at least two exons comprising coding sequence;
   instructions for practicing a method of screening for compounds that inhibit translation termination at premature stop codons and nonsense mediated RNA decay; and
   a control compound that inhibits translation termination and nonsense-mediated RNA decay.

18. The kit of claim 17, wherein the control compound is G418or gentamycin sulfate.

19. The kit of claim 17, wherein the premature stop codon is located in a last exon.

20. The kit of claim 17, wherein the nucleic acid encodes luciferase, green fluorescent protein, red fluorescent protein, phosphatase, peroxidase, kinase, chloramphenicol transferase, or β-galactosidase.

21. The method of claim 1, wherein contacting the cell with the candidate compound increases the amount of RNA comprising the premature stop codon that is present in the cell.

* * * * *